United States Patent
Geissler

(10) Patent No.: US 6,215,006 B1
(45) Date of Patent: Apr. 10, 2001

(54) PROCESS FOR THE PREPARATION OF 3-ISOCHROMANOES BY CYCLIZATION OF O-CHLOROMETHYLPHENYLACETIC ACIDS

(75) Inventor: Holger Geissler, Mainz (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/574,332

(22) Filed: May 19, 2000

(30) Foreign Application Priority Data

May 21, 1999 (DE) .............................. 199 23 548

(51) Int. Cl.$^7$ .................................... C07D 311/74
(52) U.S. Cl. ........................ 549/290; 549/289; 549/280
(58) Field of Search .................. 549/280, 289, 549/290

(56) References Cited

U.S. PATENT DOCUMENTS 6,075,152 * 6/2000 Geissler et al. ....................... 549/290

FOREIGN PATENT DOCUMENTS

WO 97/12864   4/1997 (WO) .
WO 97/48692  12/1997 (WO) .

* cited by examiner

*Primary Examiner*—Amelia Owens
(74) *Attorney, Agent, or Firm*—Scott E. Hanf

(57) ABSTRACT

The present invention relates to a process for the preparation of a 3-isochromanone of the formula (I)

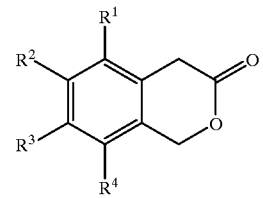

(I)

by reaction of an o-chloromethylphenylacetic acid of the formula (II)

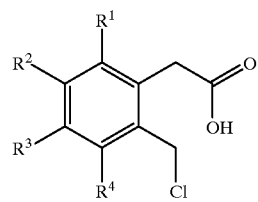

(II)

at a temperature of 100 to 250° C. in the presence or absence of an ionic halide, in the presence or absence of an organic solvent with and removal of hydrogen chloride, where in the formulae (I) and (II) the radicals $R^1$, $R^2$, $R^3$ and $R^4$ independently of one another are:

a hydrogen or fluorine atom;

an NC or $F_3C$ group;

an alkyl alkoxy or acyloxy radical, each having 1 to 18 carbon atoms; or a $C_6$–$C_{18}$-aryloxy, aryl or heteroaryl radical, 1 to 3 atoms from the group consisting of O, N and/or S being present as heteroatoms;

or in which at least two of the radicals $R^1$, $R^2$, $R^3$ and $R^4$ are linked to one another and form at least one aliphatic or aromatic ring having 5 to 18 carbon atoms.

9 Claims, No Drawings

PROCESS FOR THE PREPARATION OF 3-ISOCHROMANOES BY CYCLIZATION OF O-CHLOROMETHYLPHENYLACETIC ACIDS

BACKGROUND OF THE INVENTION

The present invention relates to a novel, advantageous process for the preparation of 3-isochromanones by cyclization of o-chloromethylphenylacetic acids. Isochroman-3-one is of great interest as an intermediate in the synthesis of pharmaceuticals and plant protection agents.

WO 97/12864 discloses, for example, the use of 3-isochromanone as an intermediate in the preparation of fungicides and pesticides and WO 97/48692 discloses the use of 3-isochromanone in the preparation of certain agricultural products.

3-Isochromanone is a known compound and a large number of methods for preparation are mentioned in WO 97/48692. For example, 3-isochromanone can be prepared by Baeyer-Villiger oxidation of 2-indanone using hydrogen peroxide in sulfuric acid and acetic anhydride or using m-chloroperbenzoic acid in combination with trifluoroacetic acid or by reaction of bromomethylphenylacetic acid with KOH in ethanol with ring-closure.

WO 97/48692 discloses a synthesis of 3-isochromanone by chlorination of o-methylphenylacetic acid with sulfuryl chloride in the presence of free radical initiators and by subsequent reaction of the resulting 2-chloromethylphenylacetic acid with a base. The disadvantage of this process is the formation of one equivalent of salt per equivalent of 3-isochromanone in the reaction of 2-chloromethylphenylacetic acid using a base and the handling of reaction mixtures containing salts.

SUMMARY OF THE INVENTION

A need therefore exists for a process which does not have the disadvantages mentioned, is suitable for industrial implementation and produces 3-isochromanone in good yield.

DESCRIPTION OF THE PREFERRED EMBODIMENTS

This object is achieved by a process for the preparation of a 3-isochromanone of the formula (I)

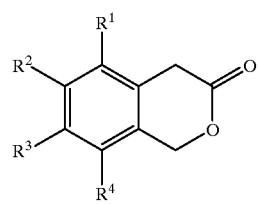
(I)

by reaction of an o-chloromethylphenylacetic acid of the formula (II)

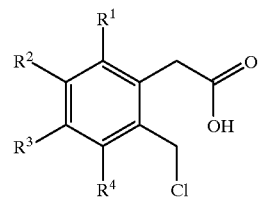
(II)

at a temperature of 100 to 250° C. in the presence or absence of an ionic halide, in the presence or absence of an organic solvent and with removal of hydrogen chloride, where in the formulae (I) and (II) the radicals $R^1$, $R^2$, $R^3$ and $R^4$ independently of one another are:
a hydrogen or fluorine atom;
an NC or $F_3C$ group;
an alkyl, alkoxy or acyloxy radical, each having 1 to 18 carbon atoms; or a $C_6$–$C_{18}$-aryloxy, aryl or heteroaryl radical, 1 to 3 atoms from the group consisting of O, N and/or S being present as heteroatoms;
or in which at least two of the radicals $R^1$, $R^2$, $R^3$ and $R^4$ are linked to one another and form at least one aliphatic or aromatic ring having 5 to 18 carbon atoms.

Surprisingly and contrary to the instructions from the literature (WO 97/48692) for bringing about the ring-closure reaction of bromo/chloromethylphenylacetic acid by addition of a base, by the process according to the invention 3-isochromanones are obtained by reaction of o-chloromethylphenylacetic acid of the formula (II) with ring closure in the absence of a base.

In this connection, the o-chloromethylphenylacetic acid is not converted into the corresponding salt of the o-chloromethylphenylacetic acid by reaction with a base and the corresponding 3-isochromanone is not formed from the salt by cyclization, but presumably the hydrogen chloride is eliminated directly from the o-chloromethylphenylacetic acid with simultaneous ring closure and formation of the corresponding 3-isochromanone.

The reaction thus proceeds not via a salt of the o-chloromethylphenylacetic acid as an intermediate which is then cyclized, but leads to the corresponding 3-isochromanone with elimination of hydrogen chloride.

The hydrogen chloride is customarily removed from the reaction mixture thermally according to its formation. It is possible to evaporate the hydrogen chloride or a mixture containing the hydrogen chloride and the organic solvent from the reaction mixture, which can contain an organic solvent. If a mixture of this type is separated, it is recommended to condense the organic solvent, to separate the hydrogen chloride and, if desired, to feed back the solvent freed from the hydrogen chloride into the reaction again.

The radicals $R^1$, $R^2$, $R^3$ and $R^4$ are, independently of one another, in particular hydrogen, fluorine, $C_1$–$C_4$-alkyl or $C_1$–$C_4$-alkoxy, preferably hydrogen, fluorine, $C_1$–$C_4$-n-alkyl or $C_1$-$C_4$-n-alkoxy, or two of the radicals $R^1$, $R^2$, $R^3$ and $R^4$ are linked to one another and form an aliphatic or aromatic ring having 5 to 10 carbon atoms.

Preferably $R^1$, $R^2$, $R^3$ and $R^4$ independently of one another are hydrogen, fluorine or $C_1$–$C_4$-alkyl, in particular hydrogen, fluorine or $C_1$–$C_4$-n-alkyl.

In the formulae (I) and (II), according to a particular embodiment two, three or four, in particular three or four, of the radicals $R^1$, $R^2$, $R^3$ and $R^4$ are hydrogen.

As mentioned at the beginning, the process can be carried out in the presence or absence of an ionic halide.

Customarily, the ionic halide is an alkali metal, ammonium or phosphonium halide, in particular an alkali metal or ammonium halide, halide having the meaning chloride, bromide or iodide, in particular iodide or bromide.

The ionic halide employed can be ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide.

As a rule, the ionic halide is employed in an amount from 0.005 to 0.5 equivalents, in particular from 0.01 to 0.05 equivalents, per equivalent of o-chloromethylphenylacetic acid employed.

It may be pointed out here that the presence of the ionic halide can be dispensed with and the process can be carried out, in particular, in the absence of the ionic halide.

As a rule, the reaction is carried out at a pressure of 10 Pa to 0.5 MPa, in particular at 100 Pa to 0.2 MPa, preferably at 1000 Pa to 0.12 MPa.

The reaction is carried out—as already mentioned at the beginning—at a temperature of 100 to 250° C., in particular 120 to 220° C., preferably 150 to 200° C. The pressure and temperature are selected such that the hydrogen chloride formed in the reaction is obtained in gaseous form and can be separated from the reaction mixture in the gaseous state.

As mentioned at the beginning, the process can be carried out in the presence or absence of an organic solvent.

Suitable organic solvents are, in particular, dipolar aprotic solvents such as dioxane, tetrahydrofuran, an N-($C_1$–$C_{18}$-alkyl)pyrrolidone, ethylene glycol dimethyl ether, a $C_1$–$C_4$-alkyl ester of an aliphatic $C_1$–$C_6$-carboxylic acid, a $C_1$–$C_6$-dialkyl ether, an N,N-di($C_1$–$C_4$-alkyl)amide of an aliphatic $C_1$–$C_4$-carboxylic acid, sulfolane, a 1,3-di($C_1$–$C_8$-alkyl)-2-imidazolidinone, an N-($C_1$–$C_8$-alkyl)caprolactam, an N,N,N',N'-tetra($C_1$–$C_8$-alkyl)urea, a 1,3-di-($C_1$–$C_8$-alkyl)-3,4,5,6-tetrahydro-2(1H)-pyrimidone, an N,N,N',N'-tetra-($C_1$–$C_8$-alkyl)sulfamide, 4-formylmorpholine, 1-formylpiperidine or 1-formylpyrrolidine, preferably an N-($C_1$–$C_{18}$-alkyl)pyrrolidone, particularly preferably N-methylpyrrolidone, N-octylpyrrolidone, N-dodecylpyrrolidone, very particularly preferably N-methylpyrrolidone. Mixtures of solvents can also be used.

In a preferred embodiment of the process according to the invention, the pressure and temperature are selected such that the solvent employed boils. The evaporated solvent is condensed, separated from the hydrogen chloride and customarily fed back into the reaction.

The hydrogen chloride formed in the reaction as a rule escapes in gaseous form from the reaction mixture and in conventional processes can be recovered by means of absorption and employed again. Thus, by absorption of gaseous hydrogen chloride in water an aqueous hydrochloric acid which can be employed in other industrial processes is obtained. When using organic solvents, the removal of the gaseous hydrogen chloride takes place particularly easily at the boiling point of the organic solvent employed. Thus the reaction can be carried out particularly readily, for example, in boiling N-methylpyrrolidone at 160° C. and 0.025 MPa.

The duration of the reaction depends, inter alia, on the reaction temperature and, when using an organic solvent, on the solubility of the hydrogen chloride in the solvent employed at the corresponding reaction temperature.

During the reaction, provision is made for thorough mixing in order to guarantee a rapid course of reaction.

The process according to the invention is suitable both for continuous and batchwise implementation.

The following experimental section describes the invention in greater detail, without restricting it.

EXAMPLES

Experimental section

Example 1

The reaction apparatus consists of a reaction vessel (1 liter glass vessel), equipped with a stirrer, a column (25 cm) packed with Raschig rings, a reflux condenser (condensing device) arranged above the column and a scrubbing column connected to the reflux condenser via a line, in which gaseous hydrogen chloride is passed in from below, while water is passed through in countercurrent flow from above in order to absorb hydrogen chloride with formation of aqueous hydrochloric acid. The aqueous hydrochloric acid is withdrawn at the bottom of the scrubbing column. The top of the scrubbing column is connected to a vacuum pump.

Carrying out the reaction:

46.0 g of o-chloromethylphenylacetic acid are dissolved in 415 g of N-methylpyrrolidone in the reaction vessel and stirred at a temperature of 160° C. and 0.025 MPa for 6 hours. The temperature in the reflux condenser is adjusted to 80° C. and the pressure is kept constant at 0.025 MPa by means of the vacuum pump. Gaseous hydrogen chloride reaches the reflux condenser together with evaporated solvent via the column packed with Raschig rings, where condensable components condense and flow back into the reaction vessel, while gaseous hydrogen chloride is fed to the scrubbing column connected downstream. An HPLC analysis of the reaction mixture shows that the reaction mixture contains 31.9 g of 3-isochromanone (yield 86.5%).

For working-up, after termination of the reaction the solvent N-methylpyrrolidone is evaporated from the reaction mixture at 100° C. and 20 hPa and the resulting 3-isochromanone is then distilled from the bottom at 160° C. and 5 hPa (head temperature 144° C.). 30.3 g of 3-isochromanone are obtained (yield 82%).

What is claimed is:

1. A process for the preparation of a 3-isochromanone of the formula (I)

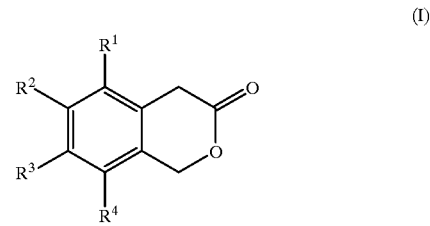

by reaction of an o-chloromethylphenylacetic acid of the formula (II)

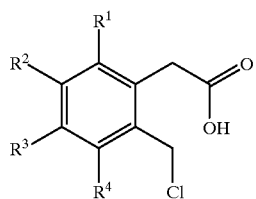

at a temperature of 100 to 250° C. in the presence or absence of an ionic halide, in the presence or absence of an organic solvent and with removal of hydrogen chloride, where in the formulae (I) and (II) the radicals $R^1$, $R^2$, $R^3$ and $R^4$ independently of one another are:

a hydrogen or fluorine atom;

an NC or $F_3C$ group;

an alkyl, alkoxy or acyloxy radical, each having 1 to 18 carbon atoms; or a $C_6$–$C_{18}$-aryloxy.

2. The process as claimed in claim 1, wherein the radicals $R^1$, $R^2$, $R^3$ and $R^4$ independently of one another are hydrogen, fluorine, $C_1$–$C_4$-alkyl or $C_1$–$C_4$-alkoxy.

3. The process as claimed in claim 1, wherein two, three or four of the radicals $R^1$, $R^2$, $R^3$ and $R^4$ are hydrogen.

4. The process as claimed in claim 1, wherein the ionic halide is an alkali metal, ammonium or phosphonium halide, halide having the meaning chloride, bromide or iodide.

5. The process as claimed in claim 1, wherein the ionic halide is ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide.

6. The process as claimed in claim 1, wherein a dipolar aprotic solvent is employed as an organic solvent.

7. The process as claimed in claim 1, wherein the dipolar aprotic solvent is dioxane, tetrahydrofuran, an N-($C_1$–$C_{18}$-alkyl)pyrrolidone, ethylene glycol dimethyl ether, a $C_1$–$C_4$-alkyl ester of an aliphatic $C_1$–$C_6$-carboxylic acid, a $C_1$–$C_6$-dialkyl ether, an N,N-di($C_1$–$C_4$-alkyl)amide of an aliphatic $C_1$–$C_4$-carboxylic acid, sulfolane, a 1,3-di($C_1$–$C_8$-alkyl)-2-imidazolidinone, an N-($C_1$–$C_8$-alkyl)-caprolactam, an N,N,N',N'-tetra($C_1$–$C_8$-alkyl)urea, a 1,3-di-($C_1$–$C_8$-alkyl)-3,4,5,6-tetrahydro-2(1H)-pyrimidone, an N,N,N',N'-tetra-($C_1$–$C_8$-alkyl)sulfamide, 4-formylmorpholine, 1-formylpiperidine or 1-formylpyrrolidine.

8. The process as claimed in claim 1, wherein the dipolar aprotic solvent is an N-($C_1$–$C_{18}$-alkyl)pyrrolidone.

9. The process as claimed in claim 1, wherein the dipolar aprotic solvent is N-methylpyrrolidone, N-octylpyrrolidone or N-dodecylpyrrolidone.

* * * * *